US012650992B2

(12) United States Patent　　(10) Patent No.:　US 12,650,992 B2
Popescu et al.　　　　　　　　　(45) Date of Patent:　　Jun. 9, 2026

(54) SYSTEMS AND METHODS FOR ANNOTATING BIOMOLECULE DATA

(71) Applicant: Life Technologies Corporation, Carlsbad, CA (US)

(72) Inventors: Liviu Popescu, Sunnyvale, CA (US); Fiona Hyland, San Mateo, CA (US)

(73) Assignee: Life Technologies Corporation, Carlsbad, CA (US)

( * ) Notice:　Subject to any disclaimer, the term of this patent is extended or adjusted under 35 U.S.C. 154(b) by 0 days.

(21) Appl. No.: 19/020,006

(22) Filed:　Jan. 14, 2025

(65)　　　　　　Prior Publication Data

US 2025/0231949 A1　　Jul. 17, 2025

Related U.S. Application Data

(63) Continuation of application No. 18/338,499, filed on Jun. 21, 2023, now abandoned, which is a continuation of application No. 17/124,846, filed on Dec. 17, 2020, now abandoned, which is a continuation of application No. 14/859,653, filed on
(Continued)

(51) Int. Cl.
| | |
|---|---|
| *G06F 16/2457* | (2019.01) |
| *G06F 16/2455* | (2019.01) |
| *G06F 16/248* | (2019.01) |
| *G16B 40/00* | (2019.01) |
| *G16B 50/00* | (2019.01) |
| *G16B 50/10* | (2019.01) |

(52) U.S. Cl.
CPC ....　*G06F 16/24573* (2019.01); *G06F 16/2455* (2019.01); *G06F 16/248* (2019.01); *G16B 40/00* (2019.02); *G16B 50/00* (2019.02); *G16B 50/10* (2019.02)

(58) Field of Classification Search
None
See application file for complete search history.

(56)　　　　　　References Cited

U.S. PATENT DOCUMENTS

| | | |
|---|---|---|
| 2003/0036087 A1 | 2/2003 | Kaushikkar et al. |
| 2003/0113727 A1 | 6/2003 | Girn et al. |
| | (Continued) | |

OTHER PUBLICATIONS

Cawsey et al., "Natural Language Generation in Health Care", Journal of the American Medical Informatics Association, vol. 4, No. 6, pp. 473-482 (1997).
(Continued)

*Primary Examiner* — Khanh B Pham
*Assistant Examiner* — Navneet Gmahl

(57)　　　　　　ABSTRACT

Systems, methods, software and computer-usable media for annotating biomolecule-related data are disclosed. In certain exemplified embodiments, the biomolecules can be nucleic acids and the data can be sequence-related data. In various embodiments, systems can include one or more public or private biological attributes (e.g., annotation information databases, data storage devices and systems, etc.) sources, one or more genomic features data sources (e.g., genomic variant tools, genomic variant databases, genomic variant data storage devices and systems, etc.), a computing device (e.g., workstation, server, personal computer, mobile device, etc.) hosting an annotations module and/or a reporting module, and a client terminal.

20 Claims, 4 Drawing Sheets

Related U.S. Application Data

Sep. 21, 2015, now abandoned, which is a continuation of application No. 13/280,990, filed on Oct. 25, 2011, now abandoned.

(60) Provisional application No. 61/482,325, filed on May 4, 2011, provisional application No. 61/406,548, filed on Oct. 25, 2010.

(56) References Cited

U.S. PATENT DOCUMENTS

| | | | |
|---|---|---|---|
| 2003/0175722 A1* | 9/2003 | Mann | G16B 50/00 |
| | | | 435/7.1 |
| 2004/0005610 A1* | 1/2004 | Sampath | G16B 20/00 |
| | | | 435/6.13 |
| 2004/0220897 A1 | 11/2004 | Bernhart et al. | |
| 2005/0032095 A1* | 2/2005 | Wigler | C07H 21/04 |
| | | | 536/24.3 |
| 2006/0020886 A1 | 1/2006 | Agrawal et al. | |
| 2006/0068405 A1 | 3/2006 | Diber et al. | |
| 2007/0027630 A1 | 2/2007 | Sanchez et al. | |
| 2007/0038385 A1* | 2/2007 | Nikolskaya | G16B 5/00 |
| | | | 702/19 |
| 2007/0169021 A1 | 7/2007 | Huynh et al. | |
| 2007/0207481 A1* | 9/2007 | Wigler | C12Q 1/6886 |
| | | | 435/6.14 |
| 2008/0228703 A1 | 9/2008 | Kenedy et al. | |
| 2009/0026082 A1 | 1/2009 | Rothberg et al. | |
| 2009/0127589 A1 | 5/2009 | Rothberg et al. | |
| 2009/0156906 A1* | 6/2009 | Liebman | G16H 50/50 |
| | | | 600/300 |
| 2009/0254572 A1 | 10/2009 | Redlich et al. | |
| 2009/0259451 A1* | 10/2009 | Senger | G16B 5/00 |
| | | | 703/11 |
| 2011/0021378 A1* | 1/2011 | Callewaert | C12N 15/81 |
| | | | 435/254.2 |
| 2011/0189663 A1* | 8/2011 | Cotterchio | C12Q 1/6886 |
| | | | 435/6.12 |
| 2011/0257896 A1* | 10/2011 | Dowds | G16B 20/10 |
| | | | 702/20 |
| 2011/0282876 A1* | 11/2011 | Tchagang | G16B 30/10 |
| | | | 707/E17.089 |
| 2011/0289441 A1* | 11/2011 | Venon | G16H 30/40 |
| | | | 715/771 |
| 2012/0102054 A1* | 4/2012 | Popescu | G16B 50/10 |
| | | | 707/754 |
| 2012/0110013 A1 | 5/2012 | Conde et al. | |
| 2013/0013213 A1 | 1/2013 | Worthey et al. | |
| 2013/0091126 A1 | 4/2013 | Krishnaswami et al. | |
| 2013/0332081 A1* | 12/2013 | Reese | G16B 20/20 |
| | | | 702/19 |
| 2014/0280327 A1 | 9/2014 | Pham et al. | |
| 2015/0095064 A1 | 4/2015 | Schols | |
| 2015/0259744 A1* | 9/2015 | Begovich | C07K 16/244 |
| | | | 424/130.1 |

OTHER PUBLICATIONS

Ge, Dongliang et al., "SVA: software for annotating and visualizing sequenced human genomes", Bioinformatics vol. 27, No. 14, 2011, 1998-2000.

Kent W., et al., "Assembly of the Working Draft of the Human Genome with GigAssembler", Genome Research, vol. 11, 2001, pp. 1541-1548.

Lee, Phil et al., "F-SNP: computationally predicted functional SNPs for disease association studies", Nucleic Acids Research vol. 36, Database issue, 2008, D820-D824.

Mullikin, J et al., "The Phusion Assembler", Genome Research, vol. 13, 2003, pp. 81-90.

PCT/US2012/059601, International Preliminary Report on Patentability, Apr. 24, 2014, 13 pages.

PCT/US2012/059601, International Search Report mailed Jul. 12, 2013, 9 pages.

PCT/US2012/059601, International Written Opinion mailed Jul. 12, 2013, 13 pages.

PCT/US2012/059601, Partial International Search Report mailed Jan. 17, 2013, 7 pages.

Pico et al., "SNPLogic: an interactive single nucleotide polymorphism selection, annotation, and prioritization system", Nucleic Acids Research, vol. 37, Database issue, pp. D803-D809 (2009).

Roach, Jet al., "Pairwise End Sequencing: A Unified Approach to Genomic Mapping and Sequencing", Genomics, vol. 26, 1995, pp. 345-353.

Sambrook et al, "Molecular Cloning: A Laboratory Manual", Third ed., Cold Spring Harbor Laboratory Press, Cold Spring Harbor, N.Y., 2000, cover pages and table of contents, 25 pages.

Siegel, Andrew et al, "Modeling the Feasibility of Whole Genome Shotgun Sequencing Using a Pairwise End Strategy", Genomics, 68, 2000, 237-246.

Torkamani et al., "Annotating individual human genomes", Genomics, vol. 98, No. 4, pp. 233-241 (2011).

Wang K., et al, "ANNOVAR: Functional Annotation of Genetic Variants From High-throughput Sequencing Data," Nucleic Acids Research, 2010, vol. 38, No. 16, pp. 1-7.

* cited by examiner

SYSTEMS AND METHODS FOR ANNOTATING BIOMOLECULE DATA

CROSS-REFERENCE TO RELATED APPLICATIONS

This application is a continuation of U.S. Ser. No. 18/338,499 filed Jun. 21, 2023, which is a continuation of U.S. Ser. No. 17/124,846 filed Dec. 17, 2020, which is a continuation of U.S. Ser. No. 14/859,653 filed Sep. 21, 2015, which is a continuation of U.S. Ser. No. 13/280,990 filed Oct. 25, 2011, which claims priority to U.S. Ser. No. 61/406,548, filed Oct. 25, 2010, and U.S. Ser. No. 61/482,325, filed May 4, 2011, the disclosures of which are hereby incorporated herein by reference in their entirety as if set forth fully herein.

FIELD

The present disclosure relates to biomolecule-related data, and in particular to systems, methods, software and computer-usable media for annotating genomic variant-related data.

INTRODUCTION

Upon completion of the Human Genome Project, one focus of the sequencing industry has shifted to finding higher throughput and/or lower cost nucleic acid sequencing technologies, sometimes referred to as "next generation" sequencing (NGS) technologies. In making sequencing higher throughput and/or less expensive, the goal is to make the technology more accessible for sequencing. These goals can be reached through the use of sequencing platforms and methods that provide sample preparation for larger quantities of samples of significant complexity, sequencing larger numbers of complex samples, and/or a high volume of information generation and analysis in a short period of time. Various methods, such as, for example, sequencing by synthesis, sequencing by hybridization, and sequencing by ligation are evolving to meet these challenges.

A wealth of nucleic acid sequence information is now available in sequence databases, both public and private. For example, public databases of metabolic, genetic and physiological pathways of various organisms (e.g., Munich Information Center for Protein Sequences (MIPS)) and some genes (e.g., Kyoto Encyclopedia of Genes and Genomes (KEGG)) have been developed largely from the published literature of many traditional low-throughput experimental studies. An advantage of this abundance of data is that improved diagnostic testing and therapeutic regimens (e.g., drugs, surgery, radiation therapy, medical devices, diet, psychiatric therapy, etc.) will be possible as new information about genetic and epigenetic correlates of disease, drug targets, protein therapeutics, devices, treatment protocols, and the like are identified and characterized. In addition, because relatively small differences in the genetic makeup (genotype), gene expression, or epigenetic status of individuals can result in large differences in physical characteristics (phenotype), some diagnostic testing and therapeutic regimens may work better with some individuals than with others, and in some cases deleterious effects can be avoided. With knowledge of how different genotypes or other genetic and epigenetic factors affect the function of a individual's various biological pathways (e.g., metabolic, signaling, regulation, etc.), diagnostic tests and treatment regimens can potentially be customized based on genetic and epigenetic information associated with the specific patient being treated.

While the quantity of nucleic acid sequence data that one can gather using conventional sequencing techniques is very large, it can often not be presented or analyzed in the most useful context. The diagnostic and therapeutic relevance of genetic and epigenetic data can often be best determined by its relationship to other pieces of information. For example, knowing that a particular genetic mutation (e.g., SNP, Indel, CNV, etc.) affects a particular metabolic or physiological pathway that plays a role in or otherwise affects the inception, progression, or treatment of a particular disease can be clinically important information. In addition, there is a need to correlate this data with various types of clinical data, for example, a patient's age, sex, weight, stage of clinical development, stage of disease progression, etc.

Conventional techniques do not facilitate easy identification of these types of candidate gene mutations. This is due to the enormous amount of information being generated by the researchers, and the lack of adequate tools to organize the information in a manner which facilitates analysis of the information. However, the information provided by the various sources of information identified above and other sources has not been integrated in a coherent manner conducive to identification of candidate genes.

As such, there is a need for annotations processing to add new attributes to the an input file adding information from publicly available sources about the genomic variants in the input, features intersecting the variants in the input file, or any biological function potentially changed by the variants.

SUMMARY

Systems, methods, software and computer-usable media for annotating biomolecule-related data are disclosed. Biomolecule-related data can relate to proteins, peptides, nucleic acids, and the like, and can include structural and functional information such as secondary or tertiary structures, amino acid or nucleotide sequences, sequence motifs, binding properties, genetic mutations and variants, and the like.

In various embodiments of this disclosure, annotations can include or be derived from public or private sources of biological attributes, sources and/or genomic features data sources. For example, sources of annotation information can include annotation information databases, data storage devices and systems, genomic variant tools, genomic variant databases, genomic variant data storage devices and systems, and the like. Systems according to this disclosure can include one or more sources of annotation information, one or more computing devices, and one or more client terminals.

Computing devices, such as workstations, servers, personal computers, mobile devices, and the like can host annotation modules, reporting modules, or both. An annotations module can include annotation components and/or analytics components, and can be configured to receive genomic features data from the genomic features data sources, search the biological attributes sources (for example, to identify relevant biological attributes) and annotate the genomic features data therewith. An analytics component can be configured to parse the annotated genomic features data to ascertain statistical trends within that data.

These and other features are provided herein.

DRAWINGS

For a more complete understanding of the principles disclosed herein, and the advantages thereof, reference is now made to the following descriptions taken in conjunction with the accompanying drawings, in which.

Figure 1:
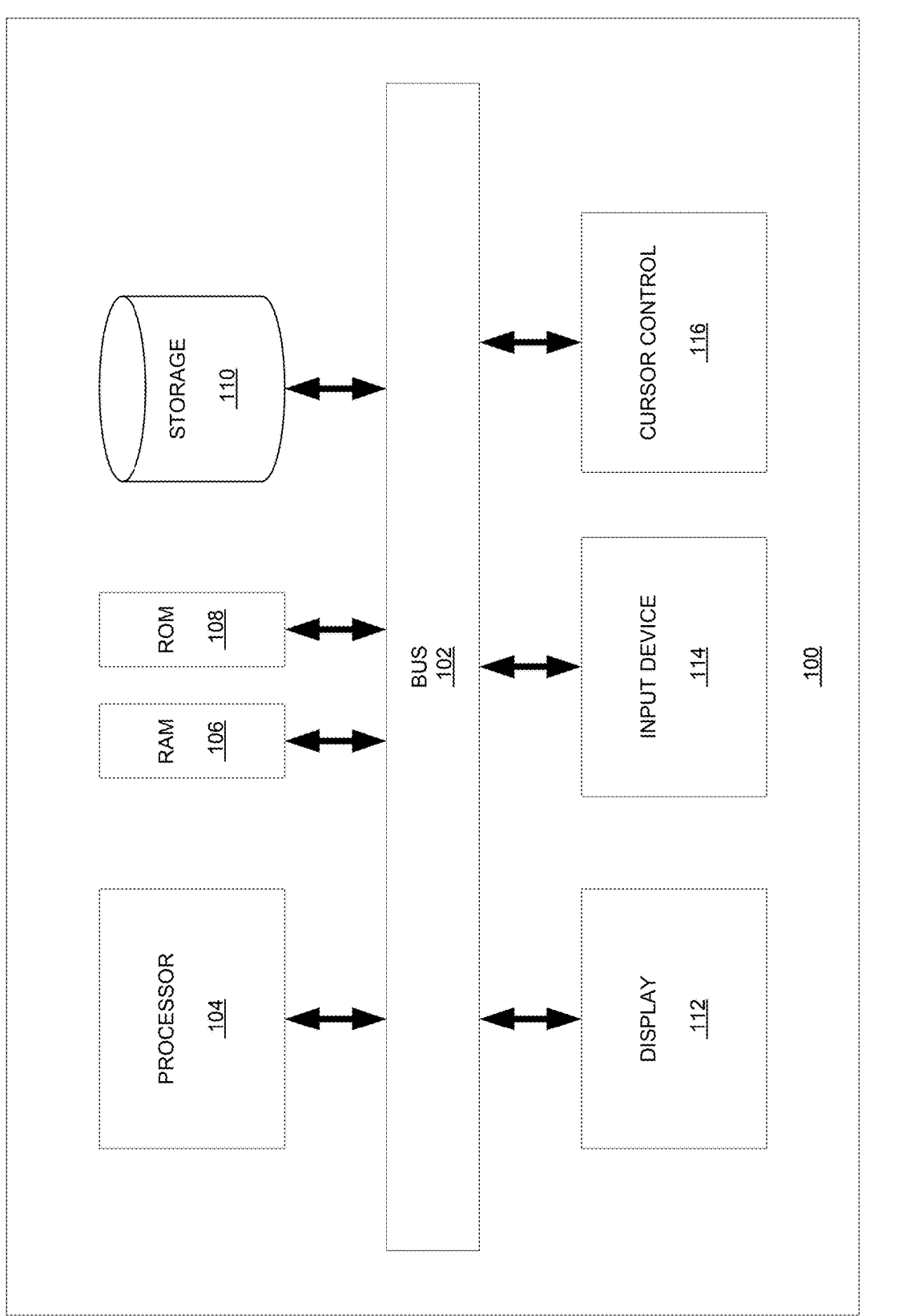
FIG. 1 is a block diagram that illustrates a computer system, in accordance with various embodiments.

It is to be understood that the figures are not necessarily drawn to scale, nor are the objects in the figures necessarily drawn to scale in relationship to one another. The figures are depictions that are intended to bring clarity and understanding to various embodiments of apparatuses, systems, and methods disclosed herein. Wherever possible, the same reference numbers will be used throughout the drawings to refer to the same or like parts. Moreover, it should be appreciated that the drawings are not intended to limit the scope of the present teachings in any way.

DESCRIPTION OF VARIOUS EMBODIMENTS

Embodiments of systems and methods for annotating genomic variants identified using gene sequencing platforms are described herein.

The section headings used herein are for organizational purposes only and are not to be construed as limiting the described subject matter in any way.

In this detailed description of the various embodiments, for purposes of explanation, numerous specific details are set forth to provide a thorough understanding of the embodiments disclosed. One skilled in the art will appreciate, however, that these various embodiments may be practiced with or without these specific details. In other instances, structures and devices are shown in block diagram form. Furthermore, one skilled in the art can readily appreciate that the specific sequences in which methods are presented and performed are illustrative and it is contemplated that the sequences can be varied and still remain within the spirit and scope of the various embodiments disclosed herein.

All literature and similar materials cited in this application, including but not limited to, patents, patent applications, articles, books, treatises, and internet web pages are expressly incorporated by reference in their entirety for any purpose. When definitions of terms in incorporated references appear to differ from the definitions provided in the present teachings, the definition provided in the present teachings shall control.

It will be appreciated that there is an implied "about" prior to the temperatures, concentrations, times, etc. discussed in the present teachings, such that slight and insubstantial deviations are within the scope of the present teachings. In this application, the use of the singular includes the plural unless specifically stated otherwise. Also, the use of "comprise", "comprises", "comprising", "contain", "contains", "containing", "include", "includes", and "including" are not intended to be limiting. It is to be understood that both the foregoing general description and the following detailed description are exemplary and explanatory only and are not restrictive of the present teachings.

Unless defined otherwise, all technical and scientific terms used herein have the same meaning as is commonly understood by one of ordinary skill in the art to which the various embodiments described herein belongs.

Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art. Standard techniques are used, for example, for nucleic acid purification and preparation, chemical analysis, recombinant nucleic acid, and oligonucleotide synthesis. Enzymatic reactions and purification techniques are performed according to manufacturer's specifications or as commonly accomplished in the art or as described herein. The techniques and procedures described herein are generally performed according to conventional methods well known in the art and as described in various general and more specific references that are cited and discussed throughout the instant specification. See, e.g., Sambrook et al., *Molecular Cloning: A Laboratory Manual* (Third ed., Cold Spring Harbor Laboratory Press, Cold Spring Harbor, N.Y. 2000). The nomenclatures utilized in connection with, and the laboratory procedures and techniques described herein are those well known and commonly used in the art.

As used herein, "a" or "an" means "at least one" or "one or more."

A "system" denotes a set of components, real or abstract, comprising a whole where each component interacts with or is related to at least one other component within the whole.

A "biomolecule" is any molecule that is produced by a living organism, including large polymeric molecules such as proteins, polysaccharides, lipids, and nucleic acids as well as small molecules such as primary metabolites, secondary metabolites, and other natural products.

The phrase "next generation sequencing" or NGS refers to sequencing technologies having increased throughput as compared to traditional Sanger- and capillary electrophoresis-based approaches, for example with the ability to generate hundreds of thousands of relatively small sequence reads at a time. Some examples of next generation sequencing techniques include, but are not limited to, sequencing by synthesis, sequencing by ligation, and sequencing by hybridization. More specifically, the Ion Torrent Personal Genome Machine (PGM) and SOLiD Sequencing System of Life Technologies Corp. provide massively parallel sequencing with enhanced accuracy. The SOLiD System and associated workflows, protocols, chemistries, etc. are described in more detail in PCT Publication No. WO 2006/084132, entitled "Reagents, Methods, and Libraries for Bead-Based Sequencing," international filing date Feb. 1, 2006, U.S. patent application Ser. No. 12/873,190, entitled "Low-Volume Sequencing System and Method of Use," filed on Aug. 31, 2010, and U.S. patent application Ser. No. 12/873,132, entitled "Fast-Indexing Filter Wheel and Method of Use," filed on Aug. 31, 2010, the entirety of each of these applications being incorporated herein by reference.

The phrase "sequencing run" refers to any step or portion of a sequencing experiment performed to determine some information relating to at least one biomolecule (e.g., nucleic acid molecule).

It is well known that DNA (deoxyribonucleic acid) is a chain of nucleotides consisting of 4 types of nucleotides; A (adenine), T (thymine), C (cytosine), and G (guanine), and that RNA (ribonucleic acid) is comprised of 4 types of nucleotides; A, U (uracil), G, and C. It is also known that certain pairs of nucleotides specifically bind to one another in a complementary fashion (called complementary base pairing). That is, adenine (A) pairs with thymine (T) (in the case of RNA, however, adenine (A) pairs with uracil (U)), and cytosine (C) pairs with guanine (G). In various embodiments, the nucleotides can be in a modified form, such as methylated C.

When a first nucleic acid strand binds to a second nucleic acid strand made up of nucleotides that are complementary to those in the first strand, the two strands bind to form a double strand. As used herein, "nucleic acid sequencing data," "nucleic acid sequencing information," "nucleic acid sequence," "genomic sequence," "genetic sequence," "fragment read," "fragment sequence," "sequence read," or "nucleic acid sequencing read" denotes any information or data that is indicative of the order of the nucleotide bases (e.g., adenine, guanine, cytosine, and thymine/uracil) in a molecule (e.g., whole genome, whole transcriptome, exome, oligonucleotide, polynucleotide, fragment, etc.) of DNA or RNA. It should be understood that the present teachings contemplate sequence information obtained using all available varieties of techniques, platforms or technologies, including, but not limited to: capillary electrophoresis, microarrays, ligation-based systems, polymerase-based systems, hybridization-based systems, direct or indirect nucleotide identification systems, pyrosequencing, ion- or pH-based detection systems, electronic signature-based systems, etc.

The phrase "ligation cycle" refers to a step in a sequence-by-ligation process where a probe sequence is ligated to a primer or another probe sequence.

The phrase "color call" refers to an observed dye color resulting from the detection of a probe sequence after a ligation cycle of a sequencing run.

The phrase "color space" refers to a nucleic acid sequence data schema where nucleic acid sequence information is represented by a set of colors (e.g., color calls, color signals, etc.) each carrying details about the identity and/or positional sequence of bases that comprise the nucleic acid sequence. For example, the nucleic acid sequence "ATCGA" can be represented in color space by various combinations of colors that are measured as the nucleic acid sequence is interrogated using optical detection-based (e.g., dye-based, etc.) sequencing techniques such as those employed by the SOLiD System. That is, in various embodiments, the SOLiD System can employ a schema that represents a nucleic acid fragment sequence as an initial base followed by a sequence of overlapping dimers (adjacent pairs of bases). The system can encode each dimer with one of four colors using a coding scheme that results in a sequence of color calls that represent a nucleotide sequence.

The phrase "base space" refers to a nucleic acid sequence data schema where nucleic acid sequence information is represented by the actual nucleotide base composition of the nucleic acid sequence. For example, the nucleic acid sequence "ATCGA" is represented in base space by the actual nucleotide base identities (e.g., A, T/or U, C, G) of the nucleic acid sequence.

The phrase "flow space" refers to a nucleic acid sequence data schema wherein nucleic acid sequence information is represented by nucleotide base identifications (or identifications of known nucleotide base flows) coupled with signal or numerical quantification components representative of nucleotide incorporation events for the nucleic acid sequence. The quantification components may be related to the relative number of continuous base repeats (e.g., homopolymers) whose incorporation is associated with a respective nucleotide base flow. For example, the nucleic acid sequence "ATTTGA" may be represented by the nucleotide base identifications A, T, G and A (based on the nucleotide base flow order) plus a quantification component for the various flows indicating base presence/absence as well as possible existence of homopolymers. Thus for "T" in the example sequence above, the quantification component may correspond to a signal or numerical identifier of greater magnitude than would be expected for a single "T" and may be resolved to indicate the presence of a homopolymer stretch of "T"s (in this case a 3-mer) in the "ATTTGA" nucleic acid sequence.

A "polynucleotide", "nucleic acid", or "oligonucleotide" refers to a linear polymer of nucleosides (including deoxyribonucleosides, ribonucleosides, or analogs thereof) joined by internucleosidic linkages. Typically, a polynucleotide comprises at least three nucleosides. Usually oligonucleotides range in size from a few monomeric units, e.g. 3-4, to several hundreds of monomeric units. Whenever a polynucleotide such as an oligonucleotide is represented by a sequence of letters, such as "ATGCCTG," it will be understood that the nucleotides are in 5'->3' order from left to right and that "A" denotes deoxyadenosine, "C" denotes deoxycytidine, "G" denotes deoxyguanosine, and "T" denotes thymidine, unless otherwise noted. The letters A, C, G, and T may be used to refer to the bases themselves, to nucleosides, or to nucleotides comprising the bases, as is standard in the art.

The techniques of "paired-end," "pairwise," "paired tag," or "mate pair" sequencing are generally known in the art of molecular biology (Siegel A. F. et al., Genomics. 2000, 68: 237-246; Roach J. C. et al., Genomics. 1995, 26: 345-353). These sequencing techniques can allow the determination of multiple "reads" of sequence, each from a different place on a single polynucleotide. Typically, the distance (i.e., insert region) between the two reads or other information regarding a relationship between the reads is known. In some situations, these sequencing techniques provide more information than does sequencing two stretches of nucleic acid sequences in a random fashion. With the use of appropriate software tools for the assembly of sequence information (e.g., Millikin S. C. et al., Genome Res. 2003, 13: 81-90; Kent, W. J. et al., Genome Res. 2001, 11: 1541-8) it is possible to make use of the knowledge that the "paired-end," "pairwise," "paired tag" or "mate pair" sequences are not completely random, but are known to occur a known distance apart and/or to have some other relationship, and are therefore linked or paired in the genome. This information can aid in the assembly of whole nucleic acid sequences into a consensus sequence.

The phrase "genomic variants" or "genome variants" denote a single or a grouping of genes that have undergone changes as referenced against a particular species or sub-populations within a particular species due to mutations, recombination/crossover or genetic drift. Examples of types of genomic variants include, but are not limited to: single nucleotide polymorphisms (SNPs), copy number variations (CNVs), insertions/deletions (Indels), inversions, etc.

Genomic variants can be identified using a variety of techniques, including, but not limited to: array-based methods (e.g., DNA microarrays, etc.) and whole or targeted nucleic acid sequencing. With nucleic acid sequencing, coverage data can be available at single base resolution. Nucleic acid sequencing systems such as the Life Technologies/Ion Torrent Personal Genome Machine (PGM) and Applied Biosystems SOLID™ Sequencing System can be used to sequence nucleic acid samples (for example human tissue/cell samples) which can include a test (or candidate) sample and a reference (or normal) sample.

In various embodiments, genomic variants can be detected using a nucleic acid sequencing system and/or analysis of sequencing data. The sequencing workflow can begin with the test sample being sheared or digested into hundreds, thousands or millions of smaller fragments which are sequenced on a nucleic acid sequencer to provide hundreds, thousands or millions of nucleic acid sequence reads. Each read can then be mapped to a reference or target genome, and in the case of mate-pair fragments, the reads can be paired thereby allowing interrogation of repetitive regions of the genome. The results of mapping and pairing can be used as input for various standalone or integrated genome variant (e.g., SNP, CNV, Indel, inversion, etc.) analysis tools.

When genome variants are initially identified in genomic DNA, especially during analysis of disease-associated genes, their functional implications might not be immediately evident. Distinguishing between a genomic variant that changes the phenotype and one that does not is a difficult task. An increasing amount of evidence indicates that genomic variants in both coding and non-coding sequences can have unexpected deleterious effects on the splicing of a gene transcript. This makes distinguishing between benign polymorphisms and disease-associated splicing mutations difficult. Therefore, the ability to link the genetic variants identified in a nucleic acid sequence to various pieces of relevant biological information can greatly assist in the determination of the biological significance of the identified genetic variants.

The phrase "functional annotation" denotes data and information that can be relevant to the role that a called variant plays in gene/transcript/protein level function.

The phrase "coding region" denotes the portion of a gene's DNA or RNA, composed of exons that codes for protein. It should be understood, however, that the coding region of mRNA does not typically include the first part of the first exon (the 5' untranslated region) or the last part of the last exon (the 3' untranslated region).

The phrase "intragenic region," "intronic region," or "intron" denotes any nucleotide sequence within a gene that is removed by RNA splicing to generate the final mature RNA product of a gene.

The phrase "intergenic region" denotes a stretch of DNA sequences located between genes that contain few or no genes.

The phrase "sample genome" can denote a whole or partial genome of an organism.

Systems and methods for annotating genetic variants (e.g., SNPs, Indels, CNVs, inversions, etc.) identified from analyzing nucleic acid sequence data with information/attributes that are relevant to the identified genetic variants, are disclosed. That is, the various embodiments disclosed herein can utilize external sources of information (i.e., annotation sources) to determine the consequences of genomic variants on cell function and whether these variants were previously observed and/or studied.

Examples of annotation sources, include, but are not limited to gene transport format (GTF) database from Reg-Gene database/UCSC (used to determine whether a variant overlaps a gene or exon), the dbSNP database/National Center for Biotechnology Information (NCBI) (contains information on SNPs and indels already found by other studies), etc. These annotations can be useful in helping to determine the potential functional consequences of the identified genomic variant.

Computer-Implemented System

FIG. 1 is a block diagram that illustrates a computer system 100, upon which embodiments of the present teachings may be implemented. In various embodiments, computer system 100 can include a bus 102 or other communication mechanism for communicating information, and a processor 104 coupled with bus 102 for processing information. In various embodiments, computer system 100 can also include a memory 106, which can be a random access memory (RAM) or other dynamic storage device, coupled to bus 102 for determining base calls, and instructions to be executed by processor 104. Memory 106 also can be used for storing temporary variables or other intermediate information during execution of instructions to be executed by processor 104. In various embodiments, computer system 100 can further include a read only memory (ROM) 108 or other static storage device coupled to bus 102 for storing static information and instructions for processor 104. A storage device 110, such as a magnetic disk or optical disk, can be provided and coupled to bus 102 for storing information and instructions.

In various embodiments, computer system 100 can be coupled via bus 102 to a display 112, such as a cathode ray tube (CRT) or liquid crystal display (LCD), for displaying information to a computer user. An input device 114, including alphanumeric and other keys, can be coupled to bus 102 for communicating information and command selections to processor 104. Another type of user input device is a cursor control 116, such as a mouse, a trackball or cursor direction keys for communicating direction information and command selections to processor 104 and for controlling cursor movement on display 112. This input device typically has two degrees of freedom in two axes, a first axis (i.e., x) and a second axis (i.e., y), that allows the device to specify positions in a plane. In various embodiments, the functionality of the cursor control 116 or input device 114 can be incorporated into display 112, such as a touch screen display.

A computer system 100 can perform the present teachings. Consistent with certain implementations of the present teachings, results can be provided by computer system 100 in response to processor 104 executing one or more sequences of one or more instructions contained in memory 106. Such instructions can be read into memory 106 from another computer-readable medium, such as storage device 110. Execution of the sequences of instructions contained in memory 106 can cause processor 104 to perform the processes described herein. Alternatively hard-wired circuitry can be used in place of or in combination with software instructions to implement the present teachings. Thus implementations of the present teachings are not limited to any specific combination of hardware circuitry and software.

The term "computer-readable medium" as used herein refers to any media that participates in providing instructions to processor 104 for execution. Such a medium can take many forms, including but not limited to, non-volatile media, volatile media, and transmission media. Examples of non-volatile media can include, but are not limited to, optical or magnetic disks, such as storage device 110. Examples of volatile media can include, but are not limited to, dynamic memory, such as memory 106. Examples of transmission media can include, but are not limited to, coaxial cables, copper wire, and fiber optics, including the wires that comprise bus 102.

Common forms of computer-readable media include non-transitory computer-readable media, such as, for example, a floppy disk, a flexible disk, hard disk, magnetic tape, or any other magnetic medium, a CD-ROM, any other optical medium, punch cards, paper tape, any other physical medium with patterns of holes, a RAM, PROM, and EPROM, a FLASH-EPROM, any other memory chip or cartridge, or any other tangible medium from which a computer can read.

Various forms of computer readable media can be involved in carrying one or more sequences of one or more instructions to processor 104 for execution. For example, the instructions can initially be carried on the magnetic disk of a remote computer. The remote computer can load the instructions into its dynamic memory and send the instructions over a telephone line using a modem. A modem local to computer system 100 can receive the data on the telephone line and use an infra-red transmitter to convert the data to an infra-red signal. An infra-red detector coupled to bus 102 can receive the data carried in the infra-red signal and place the data on bus 102. Bus 102 can carry the data to memory 106, from which processor 104 retrieves and executes the instructions. The instructions received by memory 106 may optionally be stored on storage device 110 either before or after execution by processor 104.

In accordance with various embodiments, instructions configured to be executed by a processor to perform a method are stored on a computer-readable medium. The computer-readable medium can be a device that stores digital information. For example, a computer-readable medium includes a compact disc read-only memory (CD-ROM) as is known in the art for storing software. The computer-readable medium is accessed by a processor suitable for executing instructions configured to be executed.

In accordance with various embodiments, computer implemented methods disclosed herein can be implemented by an individual computer system acting independently, or by multiple computer systems acting together. For example, two or more computer systems can work together asymmetrically, such that one computer system performs a first portion of a computer implemented method and a second computer system performs a second portion of the computer implemented method. Alternatively, two or more computer systems can operate in parallel to each perform a same portion of a computer implemented method on different portions of a data set.

Nucleic Acid Sequencing Platforms

Nucleic acid sequence data can be generated using various techniques, platforms or technologies, including, but not limited to: capillary electrophoresis, microarrays, ligation-based systems, polymerase-based systems, hybridization-based systems, direct or indirect nucleotide identification systems, pyrosequencing, ion- or pH-based detection systems, electronic signature-based systems, etc.

Figure 2:
FIG. 2 is a schematic diagram of a system for reconstructing a nucleic acid sequence, in accordance with various embodiments.
Figure 2:
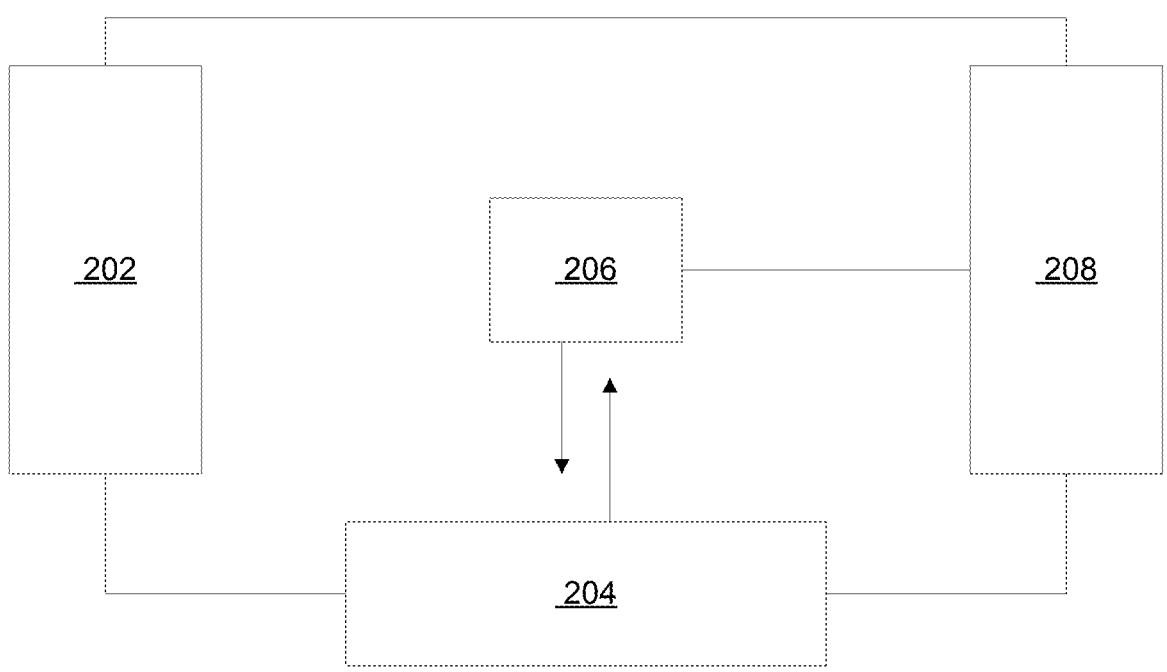

Various embodiments of nucleic acid sequencing platforms (i.e., nucleic acid sequencer) can include components as displayed in the block diagram of FIG. 2. According to various embodiments, sequencing instrument 200 can include a fluidic delivery and control unit 202, a sample processing unit 204, a signal detection unit 206, and a data acquisition, analysis and control unit 208. Various embodiments of instrumentation, reagents, libraries and methods used for next generation sequencing are described in U.S. Patent Application Publication No. 2007/066931(ASN 11/737308) and U.S. Patent Application Publication No. 2008/003571 (ASN 11/345,979) to McKernan, et al., which applications are incorporated herein by reference. Various embodiments of instrument 200 can provide for automated sequencing that can be used to gather sequence information from a plurality of sequences in parallel, i.e., substantially simultaneously.

In various embodiments, the fluidics delivery and control unit 202 can include reagent delivery system. The reagent delivery system can include a reagent reservoir for the storage of various reagents. The reagents can include RNA-based primers, forward/reverse DNA primers, oligonucleotide mixtures for ligation sequencing, nucleotide mixtures for sequencing-by-synthesis, optional ECC oligonucleotide mixtures, buffers, wash reagents, blocking reagent, stripping reagents, and the like. Additionally, the reagent delivery system can include a pipetting system or a continuous flow system which connects the sample processing unit with the reagent reservoir.

In various embodiments, the sample processing unit 204 can include a sample chamber, such as flow cell, a substrate, a micro-array, a multi-well tray, or the like. The sample processing unit 204 can include multiple lanes, multiple channels, multiple wells, or other means of processing multiple sample sets substantially simultaneously. Additionally, the sample processing unit can include multiple sample chambers to enable processing of multiple runs simultaneously. In particular embodiments, the system can perform signal detection on one sample chamber while substantially simultaneously processing another sample chamber. Additionally, the sample processing unit can include an automation system for moving or manipulating the sample chamber.

In various embodiments, the signal detection unit 206 can include an imaging or detection sensor. For example, the imaging or detection sensor can include a CCD, a CMOS, an ion sensor, such as an ion sensitive layer overlying a CMOS, a current detector, or the like. The signal detection unit 206 can include an excitation system to cause a probe, such as a fluorescent dye, to emit a signal. The expectation system can include an illumination source, such as arc lamp, a laser, a light emitting diode (LED), or the like. In particular embodiments, the signal detection unit 206 can include optics for the transmission of light from an illumination source to the sample or from the sample to the imaging or detection sensor. Alternatively, the signal detection unit 206 may not include an illumination source, such as for example, when a signal is produced spontaneously as a result of a sequencing reaction. For example, a signal can be produced by the interaction of a released moiety, such as a released ion interacting with an ion sensitive layer, or a pyrophosphate reacting with an enzyme or other catalyst to produce a chemiluminescent signal. In another example, changes in an electrical current can be detected as a nucleic acid passes through a nanopore without the need for an illumination source.

In various embodiments, data acquisition analysis and control unit 208 can monitor various system parameters. The system parameters can include temperature of various portions of instrument 200, such as sample processing unit or reagent reservoirs, volumes of various reagents, the status of various system subcomponents, such as a manipulator, a stepper motor, a pump, or the like, or any combination thereof.

It will be appreciated by one skilled in the art that various embodiments of instrument 200 can be used to practice variety of sequencing methods including ligation-based methods, sequencing by synthesis, single molecule methods, nanopore sequencing, and other sequencing techniques. Ligation sequencing can include single ligation techniques, or change ligation techniques where multiple ligation are performed in sequence on a single primary nucleic acid sequence strand. Sequencing by synthesis can include the incorporation of dye labeled nucleotides, chain termination, ion/proton sequencing, pyrophosphate sequencing, or the like. Single molecule techniques can include continuous sequencing, where the identity of the nuclear type is determined during incorporation without the need to pause or delay the sequencing reaction, or staggered sequence, where the sequencing reactions is paused to determine the identity of the incorporated nucleotide.

In various embodiments, the sequencing instrument 200 can determine the sequence of a nucleic acid, such as a polynucleotide or an oligonucleotide. The nucleic acid can include DNA or RNA, and can be single stranded, such as ssDNA and RNA, or double stranded, such as dsDNA or a RNA/cDNA pair. In various embodiments, the nucleic acid can include or be derived from a fragment library, a mate pair library, a chromatin immuno-precipitation (ChIP) fragment, or the like. In particular embodiments, the sequencing instrument 200 can obtain the sequence information from a single nucleic acid molecule or from a group of substantially identical nucleic acid molecules.

In various embodiments, sequencing instrument 200 can output nucleic acid sequencing read data in a variety of different output data file types/formats, including, but not limited to: *.fasta, *.csfasta, *.xsq, *seq.txt, *qseq.txt, *.fastq, *.sff, *prb.txt, *.sms, *srs and/or *.qv.

Genomic Variant Annotation System

Figure 3:
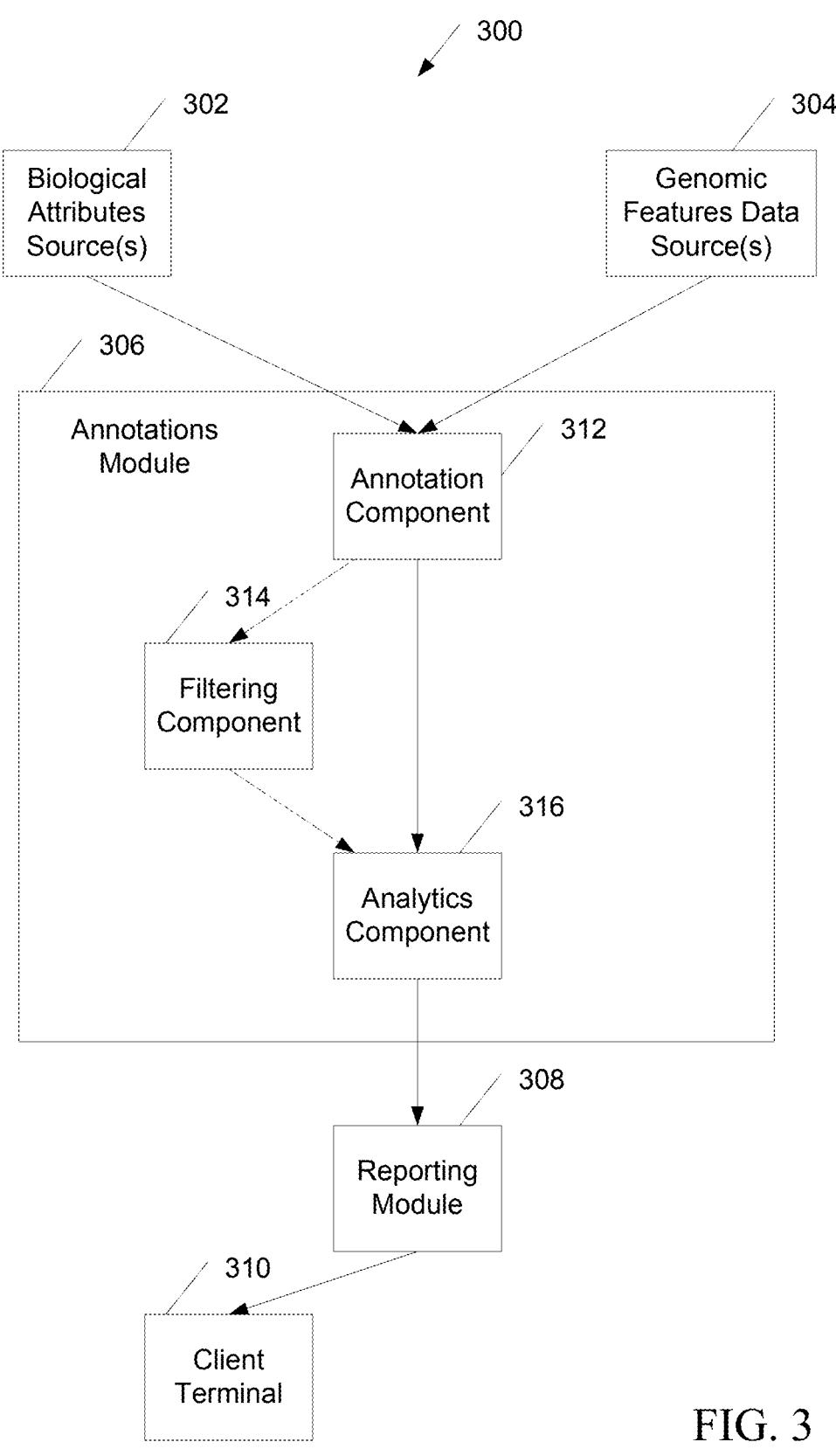
FIG. 3 is an illustration of details of a system for annotating genomic variants, in accordance with various embodiments.

FIG. 3 is a schematic diagram of a system for annotating genomic variants, in accordance with various embodiments. As depicted herein, annotation system 300 can include a genomic features data source 304, a biological attributes source 302, an annotations module 306, reporting module 308 and client terminal 310.

Biological attributes source 302 can be any private or public data store or data storage system that can be configured to store information (i.e., biological attributes) that can be relevant to functionally classifying or characterizing a genomic variant or other biological attributes. Examples of information that may be relevant to genomic variants can include, but are not limited to: information regarding inter-relationships between different genomic variants, information regarding correlations (direct or indirect) between genomic variants and disease states, information regarding correlations between genomic variants and therapeutic regimen for various disease states, information regarding correlations between the genomic variants and their position on a particular locus/chromosome, information regarding correlations between genomic variants and biological function/ processes (e.g., metabolic pathways, signaling/regulatory pathways, etc.), etc.

In various embodiments, biological attributes source 302 can be implemented as a database storage device or system that is configured to organize and store biological attribute data such that the data can be searched and retrieved manually (i.e., by a database administrator/client operator) or automatically by way of a computer program/application/ software script that can be configured to search the biological attributes source 302 for relevant information. Examples of biological attributes sources, include, but are not limited to: the RefGene Database (UCSC), the Alternative Splicing Database (EBI), the dbSNP database (NCBI), the Genomic Structural Variation database (NCBI), the GENCODE database (UCSC), the PolyPhen database (Harvard), the SIFT database (NCBI), the 3000 Genomes Project database, the Database of Genomic Variants database (EBI), the Biomart database (EBI), Gene Ontology database (public), the Bio-Cyc/HumanCyc database, the KEGG pathway database, the Reactome database, the Pathway Interaction Database (NIH), the Biocarta database, PANTHER database, etc.

In various embodiments, genomic features data sources 304 can be genomic variant identification tools that are configured to process data (e.g., nucleic acid sequencing data, microarray data, etc.) to identify genomic variants (e.g., SNPs, Indels, CNVs, inversions, etc.) and output the listing of genomic variants (along with associated information data) as a data file (e.g., GFF, VCF, HDF, etc.). That is, these tools can take raw genomic data (e.g., array probe hybridization, mapped sequence read, etc.) and apply an algorithm to that data to identify genomic variants within the regions of the genome that the data represents and output a data file that summarizes their findings. In various embodiments, genomic features data can include previously identified individual genetic mutations (e.g., individual biomarkers, etc.) or sets of genetic mutations (e.g., set of biomarkers, etc.).

In various embodiments, these tools can be standalone programs, applications or scripts. For example, a CNV identification tool that can function without being integrated with another software suite or tool that pre-processes raw array probe or sequence data prior to being analyzed by the CNV identification tool. In various embodiments, these tools can be integrated programs, applications or scripts. For example, a SNP detection tool that is integrated with a nucleic acid sequence mapping tool which first assembles raw sequence read data by mapping it to a reference sequence prior to being analyzed by the SNP detection tool.

In various embodiments, genomic features data sources 304 can be implemented as a database storage device or system that can be configured to organize and store biological attribute data such that the data can be searched and retrieved manually (i.e., by a database administrator/client operator) or automatically by way of a computer program/ application/software script that can be configured to search the genomic features data source 304 to associate genetic variants to relevant biological attributes.

Annotations module 306 can be comprised of an annotation component 312, a filtering component 314 (optional), and an analytics component 316. In various embodiments, annotations module 306 can be hosted on a computing device (e.g., workstation, server, personal computer, mobile device, etc.) that can be communicatively connected to one or more genomic features data sources 304, one or more biological attributes sources 302, one or more reporting modules 306, and/or one or more client terminals 310.

In various embodiments, the computing device hosting the annotations module 306 can be communicatively connected via a network connection (e.g., Internet, LAN, WAN, VPN, etc.) to the genomic features data sources 304 and the biological attributes sources 302. In various embodiments, the network connection can be a "hardwired" physical connection. For example, the annotations module 306 hosting device can be communicatively connected (via Category 5 (CAT5), fiber optic or equivalent cabling) to a data server (not shown) that can be communicatively connected (via CAT5, fiber optic or equivalent cabling) through the Internet and to the genomic features data sources 304 and the biological attributes sources 302. In various embodiments, the network connection can be a wireless network connection (e.g., Wi-Fi, WLAN, etc.). For example, utilizing an 802.11b/g or equivalent transmission format. In practice, the network connection utilized is dependent upon the particular requirements of the system 300.

The annotation component 312 can be configured to receive genomic features data from the genomic features data sources 304. In various embodiments, the annotation component 312 can either search the genomic features data source 304 for genomic variants information that it later receives or be supplied with data files (e.g., GFF, VCF, HDF, etc.)/data links (e.g., API link or hyperlink to a data source) containing genomic variant information.

Once the genomic features data is received, the annotation component 312 can be further configured to search one or more biological attributes data sources 302 to identify relevant biological attributes (and related information) associated with the genomic features data. In various embodiments, relevance can be based on whether the genomic feature is a marker for the biological attribute. For example, biological attributes such as a disease state or a therapeutic outcome (from drugs, surgery, radiation therapy, medical devices, diet, psychiatric therapy, etc.) are relevant to genomic features that function as markers (or indicators) for those attributes. Therefore, the annotation component 312 can identify all disease states or therapeutic outcomes (and associated information) for which a genomic feature can serve as a marker.

In various embodiments, relevance can be based on an effect that the genomic feature has on the biological attribute. That is, biological attributes are relevant to any genomic feature which can effectuate an initiating, blocking stimulatory or inhibitory response on them. Examples of these types of biological attributes which can be effectuated by a genomic feature, include, but are not limited to, biological functions such as metabolic pathways, biological signaling pathways, biological regulation pathways, etc. Therefore, annotations component 312 can identify all biological functions (and associated information) which the genomic feature can effectuate.

In various embodiments, relevance can be based on a correlation between the genomic feature and its position on a biological attribute indicating its location on a particular locus/chromosome. For example, the biological attribute can be the chromosomal location of a genomic feature such as a SNP.

In various embodiments, the annotation component 312 can be configured to search one or more biological attributes data sources 302 to identify other relevant biological attributes that are relevant to the already identified relevant biological attributes based on the same associations and/or correlations as those discussed above with respect to determination of relevance to genomic features. For example, a SNP or CNV (genomic feature) can be annotated with information relating to a metabolic pathway (biological attribute) which can then be further annotated with biological attribute information relating to signaling pathways that regulate, initiate or inhibit the metabolic pathway.

Once the relevant biological attributes (and associated information) have been identified for each genomic feature (or biological attribute associated with the genomic feature), the annotation component 312 can annotate the genomic feature data file or record (that a data link points to) with the identified biological attribute (and associated information). In various embodiments, the annotations are new fields added onto the data files or data records that the data links point to. In various embodiments, the annotations are in the form of additions to metadata that is either part of or associated with the data files or data records that the data links point to.

Analytics component 316 can be configured to parse the annotated genomic features data files or records to ascertain statistical trends within the data. In various embodiments, the analytics component 316 can analyze the annotated genomic features data to ascertain statistical trends relating to the overall incidence of each particular type of genomic feature found in the genomic features data file. For example, the analytics component 316 can identify the number of a particular type of genomic variant in total or per allele/chromosome. In various embodiments, the analytics component 316 can analyze the annotated genomic features data to ascertain statistical trends relating to the annotation of the various genomic features with biological attributes. For example, the analytics component 316 can identify the number of genomic features associated with a particular metabolic pathway.

Reporting module 308 can be configured to generate a report that summarizes the annotated genomic features data and the ascertained statistical trends. For example, the reporting module 308 can generate a list of genes that have at least one overlapping genomic feature. In various embodiments, reporting module 306 can be an integrated component of annotations module 306. For example, the functions of the reporting module 308 can be provided by a component of annotations module 306. In various embodiments, reporting module 308 can be hosted on client terminal 310. In various embodiments, reporting module 308 can be hosted on a dedicated computing device that is separate and distinct from the client terminal 310 and the device hosting the annotations module 306.

Filtering component 314 can be configured to filter out annotated genomic features based on one or more conditions. Examples of these conditions, include, but are not limited to: filtering out all annotated genomic features that don't overlap an exon, filtering out all annotated genomic features that don't overlap a gene, filtering out all annotated genomic features that are not associated with a biological attribute found on a particular biological attribute source 302, and combinations thereof.

Client terminal 310 can be a thin client or thick client computing device. In various embodiments, client terminal 310 can have a web browser (e.g., INTERNET EXPLORER™, FIREFOX™, SAFARI™, etc) that can be used to control the operation of the annotations module 306 and/or reporting module 308. That is, the client terminal 310 can access the annotations module 306 using a browser to control the operation of the annotations module 306. For example, the client terminal 310 can be used to toggle the filtering component 314 on or off, depending on the requirements of the particular application. Similarly, client terminal 310 can access the reporting module 308 using a browser to control the content or format of the summary reports generated by the reporting module 308. In various embodiments, the biological attributes source 302 and/or the genomic features data source 304 can be hosted on client terminal 310.

It should be understood, however, that the various components, engines and modules hosted depicted in FIG. 3 can be combined or collapsed into a single engine, component or module, depending on the requirements of the particular application or system architecture. Moreover, in various embodiments, the annotations module 306 can comprise additional engines or components as needed by the particular application or system architecture.

Figure 4:
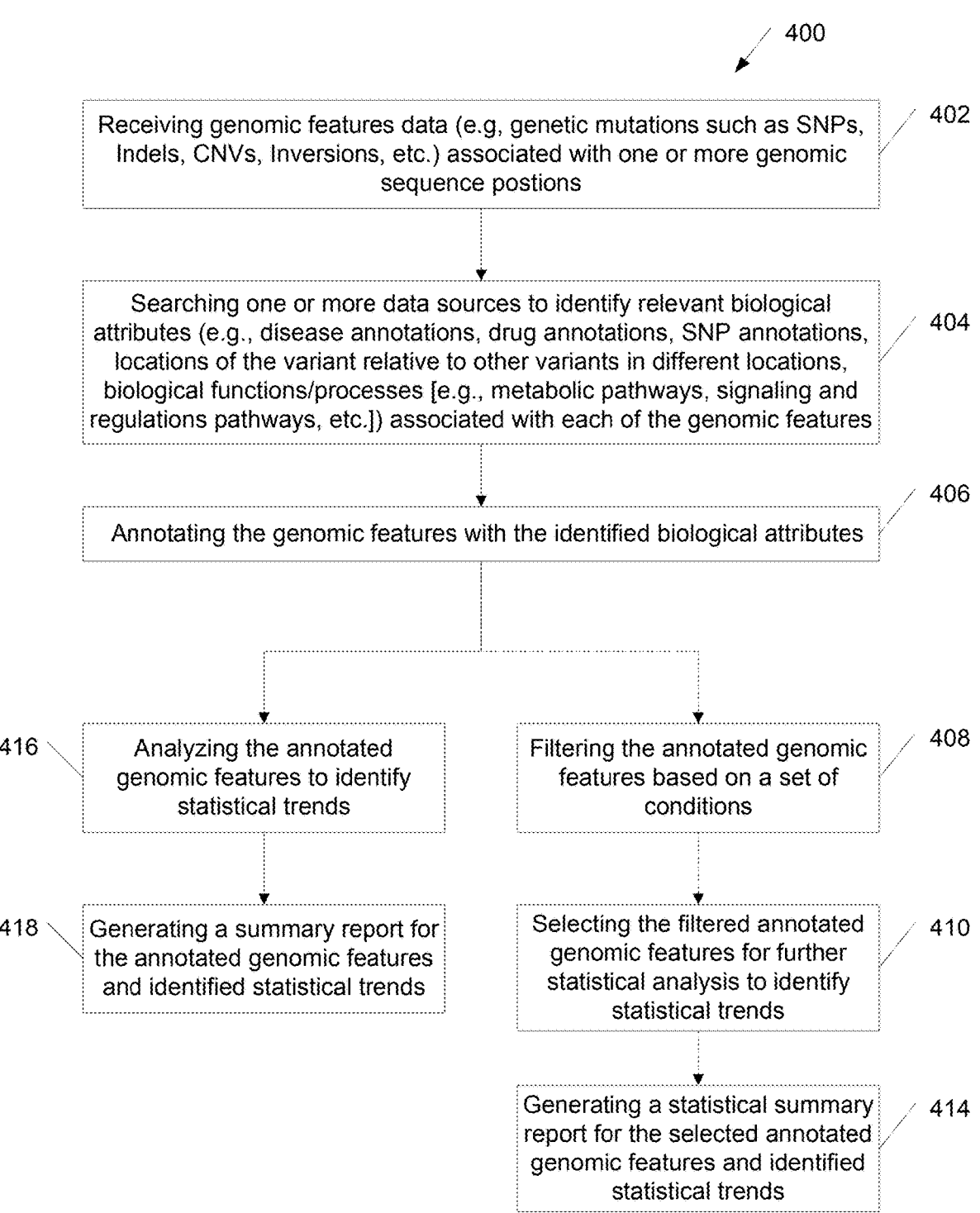
FIG. 4 is an exemplary flowchart showing a method for annotating genomic variants, in accordance with various embodiments.

FIG. 4 is an exemplary flowchart showing a method for annotating genomic variants, in accordance with various embodiments. As depicted herein, the method 400 begins with step 402 where genomic features data associated with one or more genomic sequence positions are received. In various embodiments, the genomic features data is received in the form of data files (e.g., GFF, VCF, HDF, etc.) or data links (e.g., API link or hyperlink to a data source) containing genomic variant information. In various embodiments, the data files or data links are generated by genomic variant identification tools that are configured to process genome data (e.g., nucleic acid sequencing data, microarray data, etc.) to identify genomic variants (e.g., SNPs, Indels, CNVs, inversions, etc.) and output the listing of genomic variants (along with associated information data) as a data file (e.g., GFF, VCF, HDF, etc.). That is, these tools can take raw genomic data (e.g., array probe hybridization, mapped sequence read) and apply an algorithm to that data to identify genomic variants within the regions of the genome that the data represents and output a data file that summarizes their findings. In various embodiments, genomic features data can include previously identified individual genetic mutations (e.g., individual biomarkers, etc.) or sets of genetic mutations (e.g., set of biomarkers, etc.).

In step 404, one or more data sources can be searched to identify relevant biological attributes associated with each of the genomic features. As discussed above, in various embodiments, relevance can be based on whether the genomic feature is a marker for the biological attribute. For example, biological attributes such as a disease state or a therapeutic outcome (from drugs, surgery, radiation therapy, medical devices, diet, psychiatric therapy, etc.) are relevant to genomic features that function as markers (or indicators) for those attributes.

In various embodiments, relevance can be based on an effect that the genomic feature has on the biological attribute. That is, biological attributes are relevant to any genomic feature which can effectuate an initiating, blocking stimulatory or inhibitory response on them. Examples of these types of biological attributes which can be effectuated by a genomic feature, include, but are not limited to, biological functions such as metabolic pathways, biological signaling pathways, biological regulation pathways, etc.

In various embodiments, relevance can be based on a correlation between the genomic feature and its position on a biological attribute indicating its location on a particular locus/chromosome. For example, the biological attribute can be the chromosomal location of a genomic feature such as a SNP.

In various embodiments, one or more biological attributes data sources 302 can be searched to identify other relevant biological attributes that are relevant to the already identified relevant biological attributes based on the same associations and/or correlations as those discussed above with respect to determination of relevance to genomic features. For example, a SNP or CNV (genomic feature) can be annotated with information relating to a metabolic pathway (biological attribute) which can then be further annotated with biological attribute information relating to signaling pathways that regulate, initiate or inhibit the metabolic pathway.

In step 406, the genomic features (or biological attributes associated with the genomic features) can be annotated with the identified biological attributes. That is, the genomic feature data file or record (that a data link points to) can be annotated with the identified biological attribute (and associated information). In various embodiments, the annotations are new fields added onto the data files or data records that the data links point to. In various embodiments, the annotations are in the form of additions to metadata that is either part of or associated with the data files or data records that the data links point to.

In step 416, the annotated genomic features can be analyzed to identify statistical trends. In various embodiments, the annotated genomic features data can be analyzed to ascertain statistical trends relating to the overall incidence of each particular type of genomic feature found in the genomic features data file. For example, the number of a particular type of genomic variant in total or per allele/chromosome can be identified. In various embodiments, the annotated genomic features data can be analyzed to ascertain statistical trends relating to the annotation of the various genomic features with biological attributes. For example, the number of genomic features associated with a particular metabolic pathway can be identified.

In step 418, a summary report is generated for the annotated genomic features and identified statistical trends. For example, a list of genes that have at least one overlapping genomic feature can be incorporated in the summary report.

In various embodiments, method 400 can optionally include step 408 which calls for filtering the annotated features from step 406 based on a set of conditions. Examples of these conditions can include, but are not limited to: filtering out all annotated genomic features that don't overlap an exon, filtering out all annotated genomic features that don't overlap a gene, filtering out all annotated genomic features that are not associated with a biological attribute found on a particular biological attribute source 302, and combinations thereof. After filtering step 408, the method 400 can proceed to step 410 where the filtered annotated genomic features are selected for further statistical analysis to identify statistical trends. In step 414, a statistical summary report can be generated for the filtered annotated features that were selected in step 410.

In a first aspect, a system for annotating genomic features can include a client device, a first data source, a second data source, an annotation module, and a reporting module. The first data source can be configured to store genomic features data associated with one or more genomic sequence positions, and the second data source can be configured to store biological attributes data. The annotations module can be communicatively connected with the client device, the first data source and the second data source. The reporting module can be communicatively connected to the client device and the annotations module. The annotations module can include an annotation component, and an analytics component. The annotation component can be configured to receive genomic features data from the first data source, search the second data source to identify relevant biological attributes associated with the genomic features data, and annotate the genomic features data with the identified biological attributes. The analytics component can be configured to parse the annotated genomic features data to ascertain statistical trends within the annotated genomic features data. The reporting module can be configured to generate a report summarizing the annotated genomic features data and the ascertained statistical trends.

In various embodiments of the first aspect, the annotations module can further include a filtering component configured to filter the annotated genomic features based on one or more conditions. In particular embodiments, the condition can relate to whether the genomic feature overlaps an exon. In particular embodiments, the condition can relate to whether the genomic feature overlaps a gene. In particular embodiments, the condition can relate to whether the genomic feature is found on a designated data source. In particular embodiments, the designated data source can be a dbSNP database.

In various embodiments of the first aspect, relevance can be based on whether the genomic feature is a marker for the biological attribute. In particular embodiments, the biological attribute can be a disease state. In particular embodiments, the biological attribute can be a therapeutic outcome.

In various embodiments of the first aspect, relevance can be based on an effect that the genomic feature has on the biological attribute. The effect can be an initiating response. The effect can be a blocking response. The effect can be a stimulatory response. The effect can be an inhibitory response. The biological attribute can be a biological function. The biological function can be a metabolic pathway. The biological function can be a biological signaling pathway. The biological function can be a biological regulation pathway.

In various embodiments of the first aspect, relevance can be based on interrelationships between different genomic features. In various embodiments of the first aspect, relevance can be based the biological attribute providing a characterization of the genomic feature. In various embodiments of the first aspect, relevance can be based on a correlation between the genomic feature and its position on a particular locus/chromosome. In various embodiments of the first aspect, the genomic feature can be a genetic mutation.

In a second aspect, an annotations module for annotating genomic features can include an annotation component, and an analytics component. The annotation component can be configured to, receive genomic features data from a first data source, search a second data source to identify relevant biological attributes associated with the genomic features data, and annotate the genomic features data with the identified biological attributes. The analytics component can be configured to parse the annotated genomic features data to ascertain statistical trends within the annotated genomic features data.

In various embodiments of the second aspect, the annotations module can further include a filtering component configured to filter the annotated genomic features based on one or more conditions. The condition can relate to whether the genomic feature overlaps an exon. The condition can relate to whether the genomic feature overlaps a gene. The condition can relate to whether the genomic feature is found on a designated data source.

In a third aspect, a computer implemented method for annotating genomic features can include receiving genomic features data associated with one or more genomic sequence positions, searching one or more data sources to identify biological attributes associated with each of the genomic features based on a set of criteria, and annotating the genomic features data with the identified biological attributes.

In various embodiments of the third aspect, the computer implemented method can further include analyzing the annotated genomic features data to ascertain statistical trends within the annotated genomic features data, and generating a report summarizing the annotated genomic features data and the ascertained statistical trends.

In various embodiments, the relevance can be based on whether the genomic feature is a marker for the biological attribute. The biological attribute can be a disease state. The biological attribute can be a therapeutic outcome. In various embodiments, the relevance can be based on an effect that the genomic feature has on the biological attribute. The effect can be an initiating response. The effect can be a blocking response. The effect can be a stimulatory response. The effect can be an inhibitory response. The biological attribute can be a biological function. The biological function can be a metabolic pathway. The biological function can be a biological signaling pathway. The biological function can be a biological regulation pathway. In various embodiments, the relevance can be based on interrelationships between different genomic features. The relevance can be based the biological attribute providing a characterization of the genomic feature. The relevance can be based on a correlation between the genomic feature and its position on a particular locus/chromosome. The genomic feature can be a genetic mutation.

In various embodiments of the third aspect, the computer implemented method can further include filtering the annotated genomic features based on one or more conditions. The condition can relates to whether the genomic feature overlaps an exon. The condition can relates to whether the genomic feature overlaps a gene. The condition can relates to whether the genomic feature is found on a designated data source. The designated data source can be a dbSNP database.

In a forth aspect, a computer usable media can have a computer readable program code embodied therein. The computer readable program code adapted to be executed to implement a method for annotating genomic features. The method can include receiving genomic features data associated with one or more genomic sequence positions, searching one or more data sources to identify biological attributes associated with each of the genomic features based on a set of criteria and annotating the genomic features data with the identified biological attributes.

In various embodiments of the fourth aspect, the method can further include analyzing the annotated genomic features data to ascertain statistical trends within the annotated genomic features data based on a set of requirements, and generating a report summarizing the annotated genomic features data and the ascertained statistical trends.

While the present teachings are described in conjunction with various embodiments, it is not intended that the present teachings be limited to such embodiments. On the contrary, the present teachings encompass various alternatives, modifications, and equivalents, as will be appreciated by those of skill in the art.

Further, in describing various embodiments, the specification may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process should not be limited to the performance of their steps in the order written, and one skilled in the art can readily appreciate that the sequences may be varied and still remain within the spirit and scope of the various embodiments.

The embodiments described herein, can be practiced with other computer system configurations including hand-held devices, microprocessor systems, microprocessor-based or programmable consumer electronics, minicomputers, mainframe computers and the like. The embodiments can also be practiced in distributing computing environments where tasks are performed by remote processing devices that are linked through a network.

It should also be understood that the embodiments described herein can employ various computer-implemented operations involving data stored in computer systems. These operations are those requiring physical manipulation of physical quantities. Usually, though not necessarily, these quantities take the form of electrical or magnetic signals capable of being stored, transferred, combined, compared, and otherwise manipulated. Further, the manipulations performed are often referred to in terms, such as producing, identifying, determining, or comparing.

Any of the operations that form part of the embodiments described herein are useful machine operations. The embodiments, described herein, also relate to a device or an apparatus for performing these operations. The systems and methods described herein can be specially constructed for the required purposes or it may be a general purpose computer selectively activated or configured by a computer program stored in the computer. In particular, various general purpose machines may be used with computer programs written in accordance with the teachings herein, or it may be more convenient to construct a more specialized apparatus to perform the required operations.

Certain embodiments can also be embodied as computer readable code on a computer readable medium. The computer readable medium is any data storage device that can store data, which can thereafter be read by a computer system. Examples of the computer readable medium include hard drives, network attached storage (NAS), read-only memory, random-access memory, CD-ROMs, CD-Rs, CD-RWs, magnetic tapes, and other optical and non-optical data storage devices. The computer readable medium can also be distributed over a network coupled computer systems so that the computer readable code is stored and executed in a distributed fashion.

What is claimed is:

1. A system for annotating genomic features, comprising:
a client terminal;
a first data source comprising data files or data records containing genomic features data associated with one or more genomic sequence positions within one or more regions of a genome;
a second data source comprising biological attributes data; and
a processor communicatively connected with the client terminal, the first data source and the second data source, the processor configured to:
receive the genomic features data from the first data source,
search the second data source to identify one or more relevant biological attributes associated with the genomic features data received from the first data source, wherein the one or more biological attributes comprise a disease state, a therapeutic outcome, a metabolic pathway, a biological signaling pathway, a biological regulation pathway, or any combination thereof,
annotate the genomic features data associated with the one or more genomic sequence positions received from the first data source with the identified one or more biological attributes to create a data structure containing annotated genomic features data, wherein the data structure containing the annotated genomic features data includes a new field added to the data file or the data record associated with a genomic feature, the new field containing annotations representing the identified biological attributes associated with the genomic features,
parse the annotated genomic features data accessed from the data structure to ascertain statistical trends, wherein the statistical trends include a first statistical trend related to a particular type of the genomic features within the genomic features data and a second statistical trend related to a particular type of the annotations representing the identified biological attributes associated with the genomic features in the annotated genomic features data,
configure the client terminal to display filter conditions selectable by a user,
receive a set of user-selected filter conditions from the client terminal,
query the annotations representing the identified biological attributes based on the set of user-selected filter conditions to select corresponding annotated genomic features data from the data structure, and
display, at the client terminal, a report summarizing the corresponding annotated genomic features data and the ascertained statistical trends.

2. The system, as recited in claim 1, wherein the processor is further configured to filter the annotated genomic features data based on one or more conditions to create filtered annotated genomic features data.

3. The system, as recited in claim 2, wherein the one or more conditions relate to whether an annotated genomic feature overlaps an exon, whether the annotated genomic feature overlaps a gene, whether the annotated genomic feature is found in a designated data source, or any combination thereof.

4. The system, as recited in claim 3, wherein the designated data source is a dbSNP database.

5. The system, as recited in claim 1, wherein the processor is configured to identify the relevant biological attributes based on whether the genomic feature is a marker for the biological attribute, an effect that the genomic feature has on the biological attribute, interrelationships between different genomic features, the biological attribute providing a characterization of the genomic feature, a correlation between the genomic feature and its position on a particular locus/ chromosome, or any combination thereof.

6. The system, as recited in claim 5, wherein the effect is an initiating response, a blocking response, a stimulatory response, an inhibitory response, or any combination thereof.

7. The system of claim 1, wherein the annotations are included in metadata associated with the data file or the data record.

8. The system of claim 1, wherein the processor is a component of at least one of a client device, a workstation, a server, a personal computer, and a mobile device.

9. The system, as recited in claim 1, wherein the genomic feature is a genetic mutation.

10. The system, as recited in claim 1, further comprising a sequencing machine configured to generate nucleic acid sequencing data, wherein the sequencing machine is communicatively connected with a genomic variant identification tool configured to receive and convert the nucleic acid sequencing data into the genomic features data for the first data source.

11. The system, as recited in claim 10, wherein the genomic features data comprises at least one genomic variant.

12. A method for annotating genomic features, comprising:

receiving, at a processor, genomic features data associated with one or more genomic sequence positions within one or more regions of a genome, the genomics features data received from a first data source comprising data files or data records containing the genomic features data;

searching one or more data sources to identify one or more relevant biological attributes associated with each of the genomic features based on a set of criteria, wherein the one or more biological attributes comprise a disease state, a therapeutic outcome, a metabolic pathway, a biological signaling pathway, a biological regulation pathway, or any combination thereof;

annotating, using the processor, the genomic features data associated with the one or more genomic sequence positions with the identified biological attributes to create a data structure containing annotated genomic features data, wherein the data structure containing the annotated genomic features data includes a new field added to the data file or the data record associated with a genomic feature, the new field containing annotations representing the identified biological attributes associated with the genomic features;

parsing the annotated genomic features data accessed from the data structure to ascertain statistical trends, wherein the statistical trends include a first statistical trend related to a particular type of the genomic features within the genomic features data and a second statistical trend related to a particular type of the annotations representing the identified biological attributes associated with the genomic features in the annotated genomic features data;

configuring a client terminal to display filter conditions selectable by a user;

receiving a set of user-selected filter conditions from the client terminal;

querying the annotations representing the identified biological attributes based on the set of user- selected filter conditions to select corresponding annotated genomic features data from the data structure; and displaying, at the client terminal, a report summarizing the corresponding annotated genomic features data and the ascertained statistical trends.

13. The method for annotating genomic features, as recited in claim 12, wherein identifying the one or more relevant biological attributes is based on whether the genomic feature is a marker for the biological attribute, an effect that the genomic feature has on the biological attribute, interrelationships between different genomic features, the biological attribute providing a characterization of the genomic feature, a correlation between the genomic feature and its position on a particular locus/chromosome, or any combination thereof.

14. The method for annotating genomic features, as recited in claim 13, wherein the effect is an initiating response, a blocking response, a stimulatory response, an inhibitory response, or any combination thereof.

15. The method for annotating genomic features, as recited in claim 12, wherein the genomic feature is a genetic mutation.

16. The method for annotating genomic features, as recited in claim 12, further comprising:

filtering the annotated genomic features data based on one or more conditions to create filtered annotated genomic features data.

17. The method, as recited in claim 16, wherein the one or more conditions relate to whether an annotated genomic feature overlaps an exon, whether the annotated genomic feature overlaps a gene, whether the annotated genomic feature is found in a designated data source, or any combination thereof.

18. The method for annotating genomic features, as recited in claim 12, wherein the annotations are included in metadata associated with the data file or the data record.

19. The method for annotating genomic features, as recited in claim 12, wherein the processor is a component of at least one of a client device, a workstation, a server, a personal computer, and a mobile device.

20. The method for annotating genomic features, as recited in claim 12, further comprising:

sequencing at least one nucleic acid to generate nucleic acid sequencing data; and converting the nucleic acid sequencing data into the genomic features data.

\* \* \* \* \*